(12) United States Patent
Futaya et al.

(10) Patent No.: US 12,175,660 B2
(45) Date of Patent: Dec. 24, 2024

(54) METHOD, DEVICE, AND PROGRAM FOR OBTAINING INFORMATION FROM TISSUE SECTIONS FOR PATHOLOGICAL DIAGNOSIS SUPPORT

(71) Applicant: Konica Minolta, Inc., Tokyo (JP)

(72) Inventors: Etsuko Futaya, Tokyo (JP); Hideki Goda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 434 days.

(21) Appl. No.: 17/429,246

(22) PCT Filed: Feb. 6, 2020

(86) PCT No.: PCT/JP2020/004478
§ 371 (c)(1),
(2) Date: Aug. 6, 2021

(87) PCT Pub. No.: WO2020/166469
PCT Pub. Date: Aug. 20, 2020

(65) Prior Publication Data
US 2022/0138937 A1   May 5, 2022

(30) Foreign Application Priority Data
Feb. 15, 2019   (JP) .................. 2019-025027

(51) Int. Cl.
*G06K 9/00* (2022.01)
*A61B 5/00* (2006.01)
(Continued)

(52) U.S. Cl.
CPC .......... *G06T 7/0012* (2013.01); *A61B 5/0071* (2013.01); *G01N 1/30* (2013.01);
(Continued)

(58) Field of Classification Search
CPC . G06T 7/0012; G06T 7/10; G06T 7/11; G06T 7/136; G06T 7/60; G06T 7/62;
(Continued)

(56) References Cited

U.S. PATENT DOCUMENTS

| 10,529,453 B2 * | 1/2020 | Hartmann ............ G06V 20/698 |
| 11,257,209 B2 * | 2/2022 | Barnes ................. G06V 20/698 |

(Continued)

FOREIGN PATENT DOCUMENTS

| JP | H10-197522 A | 7/1998 |
| JP | 2013537969 A | 10/2013 |

(Continued)

OTHER PUBLICATIONS

PCT, Written Opinion of ISA for the corresponding application No. PCT/JP2020/004478, dated Mar. 31, 2020, with English translation.
(Continued)

*Primary Examiner* — Eric Rush
(74) *Attorney, Agent, or Firm* — LUCAS & MERCANTI, LLP

(57) ABSTRACT

There is provided an information provision method for providing support information for supporting a judgement based on information obtained from a tissue section. The method includes: obtaining a digital bright-field image of a tissue section stained to be observable in a bright field; creating an analysis score by obtaining, combining, and scoring multiple kinds of information on the bright-field image; and presenting the analysis score as the support information.

9 Claims, 6 Drawing Sheets

(51) Int. Cl.
*G01N 1/30* (2006.01)
*G01N 33/483* (2006.01)
*G01N 33/574* (2006.01)
*G02B 21/36* (2006.01)
*G06T 7/00* (2017.01)
*G06T 7/62* (2017.01)
*G06V 20/69* (2022.01)
*G16H 50/30* (2018.01)

(52) U.S. Cl.
CPC ....... *G01N 33/4833* (2013.01); *G01N 33/574* (2013.01); *G02B 21/367* (2013.01); *G06T 7/62* (2017.01); *G06V 20/69* (2022.01); *G06V 20/698* (2022.01); *G16H 50/30* (2018.01); *G06T 2207/10056* (2013.01); *G06T 2207/10064* (2013.01); *G06T 2207/30024* (2013.01); *G06T 2207/30096* (2013.01)

(58) Field of Classification Search
CPC ............. G06T 7/70; G06T 2207/10024; G06T 2207/10056; G06T 2207/10064; G06T 2207/20092; G06T 2207/20101; G06T 2207/20104; G06T 2207/20212; G06T 2207/20221; G06T 2207/30004; G06T 2207/30024; G06T 2207/30096; G06T 2207/30101; G06T 2207/30242; G01N 1/30; G01N 21/17; G01N 21/59; G01N 21/62; G01N 21/63; G01N 21/64; G01N 21/6428; G01N 21/6439; G01N 21/6447; G01N 21/6486; G01N 2021/1765; G01N 2021/177; G01N 2021/6491; G01N 33/48; G01N 33/483; G01N 33/4833; G01N 33/50; G01N 33/5005; G01N 33/5008; G01N 33/5044; G01N 33/5076; G01N 33/5082; G01N 33/5091; G01N 33/53; G01N 33/536; G01N 33/574; G01N 33/57469; G01N 33/57484; G01N 33/57492; G06V 20/69; G06V 20/695; G06V 20/698; G16H 50/30; G02B 21/0076; G02B 21/008; G02B 21/365; G02B 21/367; A61B 5/0071; A61B 6/52; A61B 6/5205
USPC ....... 382/100, 103, 128, 133, 134, 164, 165, 382/169–173, 181, 192, 224, 254, 276, 382/286, 291, 308, 312, 325; 435/4, 5, 435/6.1, 6.11, 6.14–6.19, 7.1, 7.21, 7.23, 435/7.4, 7.5, 29, 40.5, 287.1, 287.2, 435/288.7, 808; 702/19–21, 27–29, 127, 702/128, 156; 348/79, 80; 424/9.1, 9.2, 424/9.6, 572, 573; 422/82.05, 82.07–82.9
See application file for complete search history.

(56) References Cited

U.S. PATENT DOCUMENTS

| | | | | |
|---|---|---|---|---|
| 11,526,984 | B2* | 12/2022 | Barnes | G06T 7/0012 |
| 2013/0157895 | A1* | 6/2013 | Aimiya | G01N 1/30 |
| | | | | 702/19 |
| 2014/0233826 | A1* | 8/2014 | Agaian | G06T 7/13 |
| | | | | 382/133 |
| 2015/0347702 | A1* | 12/2015 | Chukka | G16H 50/30 |
| | | | | 702/19 |
| 2017/0186156 | A1* | 6/2017 | Isoda | G06T 7/0012 |
| 2020/0160032 | A1* | 5/2020 | Allen | G06T 7/0012 |

FOREIGN PATENT DOCUMENTS

| | | |
|---|---|---|
| JP | 2016518813 A | 6/2016 |
| JP | 2016530505 A | 9/2016 |
| WO | 2014140085 A1 | 9/2014 |
| WO | 2017126420 A1 | 7/2017 |

OTHER PUBLICATIONS

International Search Report for the corresponding application No. PCT/JP2020/004478 dated Mar. 31, 2020, with English translation.
Office Action dated Oct. 3, 2023 for the corresponding Japanese Application No. 2020-572199, with English translation.

* cited by examiner

METHOD, DEVICE, AND PROGRAM FOR OBTAINING INFORMATION FROM TISSUE SECTIONS FOR PATHOLOGICAL DIAGNOSIS SUPPORT

CROSS REFERENCE TO RELATED APPLICATION

This Application is a 371 of PCT/JP2020/004478 filed on Feb. 6, 2020, which claims priority of Japanese patent application no. 2019-025027 filed Feb. 15, 2019, the above applications are incorporated herein by reference.

TECHNICAL FIELD

The present disclosure relates to an information provision method, an information provision device, and a program.

BACKGROUND

Various judgments are conventionally made based on information obtained from tissue sections. For example, in a pathological diagnosis, a pathologist observes stained tissue sections with a microscope to obtain morphological information and staining information, such as changes in size and shape of a cell nucleus and changes in pattern as a tissue. Based on the information, the pathologist observes whether and how a lesion is present. The information is also used for predicting prognosis of patients based on the observation of tissue sections and for predicting efficacy of pharmaceutical products in clinics or in developing the products.

In recent years, it has been known that information on the concentration of specific cells and structures in a tissue section can be useful in pathological diagnosis and the like for making a prognosis for a patient and determining his/her future treatment plan. For example, according to Patent Literature 1, a tissue section obtained from a tumor tissue is imaged to obtain a virtual slide image, and the concentration of cells and/or blood vessels around the boundary of the tumor is measured. Patent Literature 1 shows that the measured concentration makes it possible to make a prognosis for the patient. Further, according to Patent Literature 2, the number of immune cells in a tissue section obtained from a tumor tissue is obtained. Patent Literature 2 indicates a correlation between the concentration of immune cells in the tumor tissue and a prognosis for the patient.

CITATION LIST

Patent Literature

Patent Literature 1: JP2013-537969A
Patent Literature 2: JP2016-530505A

SUMMARY OF INVENTION

Technical Problem

In conventional pathological diagnosis, it is difficult to eliminate variation in diagnosis results because the diagnosis depends on subjective judgements of pathologists. In this respect, the invention of Patent Literature 1 uses digital analysis technology of a microscope image, and therefore can guarantee objectivity as compared with diagnoses by pathologists.

On the other hand, in pathological diagnosis, regions, structures, and cell types present in a tissue section are observed comprehensively. For example, a pathologist firstly evaluates the area of a tumor region in the tissue section, secondly evaluates whether specific structures, such as blood vessels and lymphatic vessels, are present in the tissue section and the number of the specific structures. The pathologist then determines the number of tumor cells and the distance between interstitial cells and tumor cells. The pathologist observes the tissue section in such an order and utilizes the positional relationship of these cells as a basis for judgment. According to the invention in Patent Literature 1, a prognosis can be made based on the concentration of cells and/or blood vessels. However, a comprehensive judgment may not be made based on the relationship among regions, structures and cell types. The invention in Patent Literature 2 evaluates the concentration of immune cells but does not determine the relationship among regions, structures, cell types, and so forth. There is room to improve accuracy in evaluations.

The present invention has been made in view of the above issues. An object of the present invention is to provide an information provision method, an information provision device, and a program that can provide objective and accurate support information for various determinations to be made based on information obtained from tissue sections.

Solution to Problem

In order to solve the above issues, the information provision method described in claim 1 is an information provision method for providing support information, the support information for supporting a judgement based on information obtained from a tissue section, the method including: obtaining a digital bright-field image of a tissue section stained to be observable in a bright field; creating an analysis score by obtaining, combining, and scoring multiple kinds of information on the bright-field image; and presenting the analysis score as the support information.

The invention described in claim 2 is the information provision method according to claim 1, wherein the obtaining includes obtaining the bright-field image of a whole of the tissue section, the bright-field image being captured by a virtual microscope slide-creating device capable of imaging the whole tissue section.

The invention described in claim 3 is the information provision method according to claim 1 or 2, wherein the creating includes creating the analysis score by obtaining, combining, and scoring the multiple kinds of information on at least two among a region, a structure, and a cell type present in the tissue section.

The invention described in claim 4 is the information provision method according to claim 3, wherein in the creating, the obtained multiple kinds of information include information on a positional relationship of the region, the structure, and the cell type present in the tissue section.

The invention described in claim 5 is the information provision method according to claim 3 or 4, wherein the tissue section is stained with a staining reagent such that a specific biological substance present in the tissue section is observable with fluorescence, the staining reagent containing phosphor integrated dots bonded with biological substance-recognizing portions, each of the phosphor integrated dots being constituted of multiple integrated fluorescent substances, the obtaining includes further obtaining a digital fluorescent image of the tissue section, and the creating includes further obtaining information on presence or distribution of the specific biological substance from the fluorescent image, and creating the analysis score by combining and scoring the information on the specific biological substance and the multiple kinds of information.

The invention described in claim 6 is the information provision method according to any one of claims 1 to 5 that further includes visualizing a specific region by staining a biological substance present in the specific region of the tissue section with a fluorescent substance such that the biological substance is observable with fluorescence.

The invention described in claim 7 is an information provision device that provides support information for supporting a judgement based on information obtained from a tissue section, the device including: an image obtainer that obtains a digital bright-field image of a tissue section stained to be observable in a bright field; a score creator that creates an analysis score by obtaining, combining, and scoring multiple kinds of information on the bright-field image; and an information presenter that presents the analysis score as the support information.

The invention described in claim 8 is a program for a computer of an information provision device that provides support information for supporting a judgement based on information obtained from a tissue section, the program causing the computer to function as: an image obtainer that obtains a digital bright-field image of a tissue section stained to be observable in a bright field; an image creator that creates an analysis score by obtaining, combining, and scoring multiple kinds of information on the bright-field image; and an information presenter that presents the analysis score as the support information.

Advantageous Effects of Invention

The present invention can provide an information provision method, an information provision device, and a program that can provide objective and accurate support information for various determinations to be made based on information obtained from tissue sections.

DESCRIPTION OF EMBODIMENTS

First, terms used in the present invention are described as follows.
1. Region

"Region" refers to an area in which a certain amount of the same structures or cells gathers.

Among regions, "tumor region" in this embodiment refers to a region formed by a certain amount of gathering tumor cells to be described later. "Stromal region" refers to a region formed by a certain amount of gathering interstitial cells to be described later.
2. Structure "Structure" refers to a certain amount of gathering cells that perform a certain physiological activity. Examples of structures include blood vessels, lymphatic vessels, and secretory glands
3. Cell Type "Cell type" refers to a type of cell as a smallest unit that works and performs a function.

Among cell types, "tumor cell" in this embodiment refers to a cell that autonomously and excessively proliferates contrary to the biological control. Examples of "tumor cell" include "cancer cell" that forms a malignant tumor. "Interstitial cell" refers to a wide variety of cells that constitute the foundation of a tissue. Examples of the interstitial cell include immune cell, inflammatory cell, fibroblast, and endothelial cell. It is known that cancer progresses by the close interaction between cancer cells and interstitial cells.

Hereinafter, one or more embodiments of the present invention are described with reference to the drawings. However, these embodiments do not limit the present invention.

<Configuration of Pathological Diagnosis Support System 100>

Figure 1:
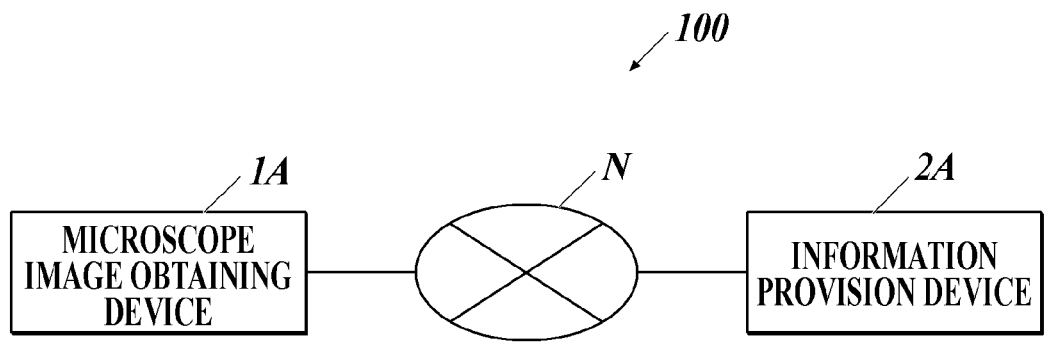
FIG. 1 shows a schematic configuration of a pathological diagnosis support system in the present invention.

FIG. 1 shows an example of overall configuration of a pathological diagnosis support system 100 that performs the information provision method in this embodiment. The pathological diagnosis support system 100 is a system that obtains and analyzes microscope images of tissue sections stained with a specific staining reagent and outputs support information.

Conventionally, various determinations/judgements, such as prediction of efficacy of a pharmaceutical product given to a living body and a pathological diagnosis/prognosis for an observation target, are made based on information on: a specific region, structure, and cell type present in a tissue section; information on the expression level of a specific biological substance present in the tissue section; and information on localized active ingredients of the pharmaceutical product given to the living body. In recent years, such determinations have been made not only by users, such as pathologists and drug development workers, but also with artificial intelligence for automatically recognizing the information. The support information in this embodiment is provided to support the improvement of the accuracy in these determinations. More specifically, the support information can take the form of analysis scores that are calculated based on information on the abundance and positions of specific regions, structures, cell types in a tissue section, and so forth. The support information serves as an objective and accurate index to support various determinations described above.

As shown in FIG. 1, the pathological diagnosis support system 100 includes a microscope image-obtaining device 1A and an information provision device 2A that are connected to each other over a communication network N for data exchange.

The pathological diagnosis support system 100 may be: a system in which the microscope image-obtaining device 1A and the information provision device 2A are placed close to each other, such as in the same building; or a system in which the microscope image-obtaining device 1A and the information provision device 2A are placed apart from each other. The communication network N is not particularly limited to a specific network, and may be over wired or wireless connection. When microscope image-obtaining device 1A and the information provision device 2A are placed close to each other, a Local Area Network (LAN) may be used, for example. When the microscope image-obtaining device 1A and the information provision device 2A are placed apart from each other, a Wide Area Network (WAN), such as the Internet, may be used, for example.

The microscope image-obtaining device 1A is a virtual-microscope-slide creating device that scans a slide on a slide fixing stage of a microscope to obtain a digital image of the whole tissue section (see, for example, JP2002-514319A). The microscope image-obtaining device 1A thus obtains image data such that the whole tissue section on the slide is viewable at one time on a display, and sends the image data to the information provision device 2A.

The microscope image-obtaining device 1A includes an irradiating unit, an image forming unit, an imaging unit, and a communication interface (I/F). The irradiating unit includes a light source and a filter. The irradiating unit irradiates, with light, the tissue section on the slide placed on the slide fixing stage. The image forming unit includes an ocular lens and an object lens. The image forming unit forms an image with transmitted light, reflected light, or fluorescent light from the irradiated tissue section on the slide. The imaging unit is a microscope-mounted camera that includes a charge coupled device (CCD) sensor. The imaging unit captures an image formed on an image forming face by the image forming unit and generates digital image data of the microscope image. The communication I/F sends the generated digital image data of the microscope image to the information provision device 2A over the communication network N. In this embodiment, the microscope image-obtaining device 1A includes: a bright field unit constituted of an irradiating unit and an image forming unit suitable for bright field observation; and a fluorescent unit constituted of an irradiating unit and an image forming unit suitable for fluorescent observation. With the bright-field unit, a bright-field image can be obtained. With the fluorescent unit, a fluorescent image can be obtained.

When the microscope image-obtaining device 1A is connected to the Internet as the communication network N, the obtained microscope image is stored in a server on the Internet so that the microscope image can be viewed on the information provision device 2A connected to the Internet.

That is, even when the microscope image-obtaining device 1A and the information provision device 2A are placed apart from each other, the user can remotely utilize, with the information provision device 2A, information obtained by the microscope image-obtaining device.

Although the microscope image-obtaining device 1A in this embodiment is the virtual-microscope-slide creating device, this is not the limitation The microscope image-obtaining device 1A may be a known microscope having a camera. The microscope having a camera can obtain a microscope image with a certain field of view for a tissue section on a slide placed on a slide fixing stage.

The information provision device 2A outputs support information generated by analyzing the microscope image transmitted from the microscope image-obtaining device 1A.

Figure 2:
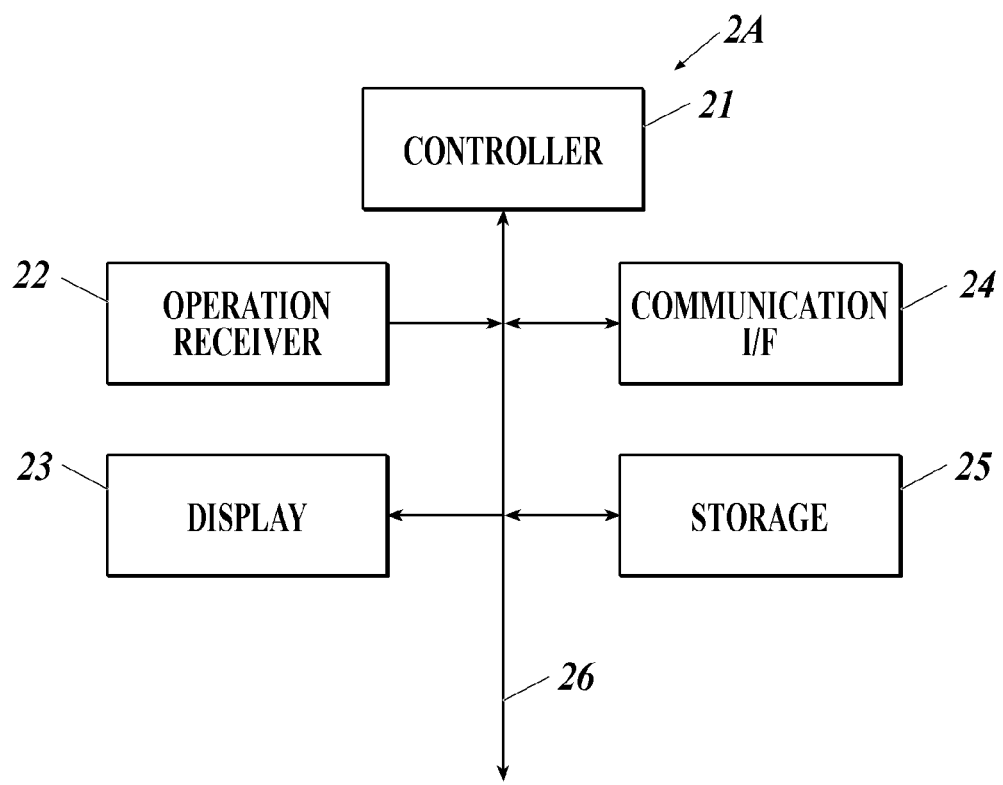
FIG. 2 is a block diagram of functional components of an information provision device in FIG. 1.

FIG. 2 shows an example of a functional configuration of the information provision device 2A. As shown in FIG. 2, the information provision device 2A includes a controller 21, an operation receiver 22, a display 23, a communication I/F 24, and a storage 25. These components are connected to each other through a bus 26.

The controller 21 includes a central processing unit (CPU) and a random access memory (RAM). The controller 21 executes various processes in cooperation with various programs stored in the storage 25 to centrally control the operation of the information provision device 2A. For example, the controller 21 serves as an image obtainer, a score creator, and an information presenter in cooperation with the programs stored in the storage 25.

The operation receiver 22 includes: a keyboard with character entry keys, numeric keys, and various function keys; and a pointing device, such as a mouse. The operation receiver 22 outputs pressing signals of a pressed key on the keyboard and operation signals of the mouse as input signals to the controller 21.

The display 23 includes a monitor, such as a cathode ray tube (CRT) and a liquid crystal display (LCD). The display 23 displays various screens in accordance with instructions of display signals input by the controller 21.

The communication I/F 24 is an interface for exchanging data with external devices including the microscope image-obtaining device 1A over the communication network N. The communication I/F 24 functions as a means to input fluorescent images, which are obtained by the microscopic image obtaining device 1A, to the information provision device 2A.

The storage 25 consists of, for example, a hard disk drive (HDD) and/or a semiconductor nonvolatile memory. The storage 25 stores various programs, various data, and so forth as described above.

The information provision device 2A may further include a LAN adapter and a router to be connected to external devices over the communication network N.

<Information Provision Method>

Hereinafter, the information provision method in this embodiment is described.

The information provision method according to the present invention is for providing support information. The support information is for supporting various determinations, such as prediction on whether a drug is efficient for an observation target, prognosis making, and pathological diagnosis of the observation target, to be made based on information obtained from a tissue section.

The information provision method according to the present invention includes at least 1: image obtaining, 2: score creating, and 3: information providing. The image obtaining is for obtaining a digitized bright-field image of a tissue section stained with a staining reagent that enables bright-field observation. The score creating is for creating analysis scores by obtaining multiple types of information from the bright-field image, combining the multiple types of information, and converting the combined information into scores. The information presenting is for presenting, to the user, the analysis scores as support information.

In addition to the above steps, the information provision method further includes 4: image obtaining for obtaining a digitized fluorescent image of the tissue section stained with phosphor integrated dots. In addition to the information obtained from the bright-field image, information obtained from the fluorescent image is also combined to create analysis scores in the score creating. This can improve accuracy of support information.

The information provision method in this embodiment includes the above steps 1 to 4, and creates the analysis scores based on the information obtained from the bright field image and the fluorescent image.

(1) Tissue Sample

A tissue sample generally takes the form of a sample slide on which a tissue section or a cell is placed. Such a sample slide is commonly used in evaluating the expression level of a specific biological substance by immunohistochemical staining. In this embodiment, a tissue section obtained from a tumor tissue is used.

The method of making the tissue sample is not particularly limited. Generally, the tissue sample can be prepared by: collecting a tissue section from a subject; fixing the tissue section with formalin or the like; dewatering the tissue section with alcohol; performing xylene processing; and immersing the tissue section in high-temperature paraffin to perform paraffin embedding; and cutting the prepared tissue sample into sections of 3 to 4 μm, for example. The obtained tissue section is then placed on a slide glass and dried to prepare a sample slide.

(2) Staining

Hereinafter, staining the tissue sample with a staining reagent is described.

(2.1) Preparation of Sample (2.1.1) Deparaffinization Treatment

The tissue section is immersed in a container with xylene to remove paraffin. Deparaffinization can be performed at room temperature, although temperature is not specifically limited. It is preferable that the immersing time be between 3 to 30 minutes. The xylene can be changed during the immersion if necessary.

Next, the tissue section is immersed in a container with ethanol to remove xylene. Deparaffinization can be performed at room temperature, although temperature is not specifically limited. It is preferable that the immersing time be between 3 to 30 minutes. The ethanol can be changed during the immersion if necessary.

The tissue section is immersed in a container with water to remove ethanol. This can be performed at room temperature, although temperature is not specifically limited. It is preferable that the immersing time be between 3 to 30 minutes. The water can be changed during the immersion if necessary.

(2.1.2) Activation Treatment

An activation treatment of the target substance is performed in accordance with a known method. This is done to stain the target substance in fluorescent staining, which is described later. Although conditions for activation are not particularly specified, an activation solution can be a buffer solution (pH 6.0) containing 0.01 M of citric acid, a solution (pH 8.0) containing 1 mM of EDTA, 5% of urea, or a buffer solution containing 0.1 M of tris hydrochloric acid, for example.

Regarding pH conditions, the activation is performed in a pH range of 2.0 to 13.0, depending on the tissue section to be used, such that a signal is issued and tissue roughness can be evaluated by the signal. The activation is usually performed in a pH range of 6.0 to 8.0. For a specific tissue section, the treatment may be performed at pH 3.0, for example.

As heating equipment, such as an autoclave, a microwave, a pressure pot, or a water bath, can be used. The activation can be performed at room temperature, although temperature is not specifically limited. The activation can be performed in 5 to 30 minutes at temperature between 50 to 130° C.

The tissue section is then immersed in a container with PBS and washed. This can be performed at room temperature, although temperature is not specifically limited. It is preferable that the immersing time be between 3 to 30 minutes. The PBS can be changed during the immersion if necessary.

(2.2) Morphological Staining

Morphological staining is performed to visualize morphologies of cells, tissues, organs, and so forth so as to be observed in a bright field.

For morphological observation of the tissue sample, eosin staining is generally used. Eosin stains cytoplasm, interstitium, various fibers, erythrocytes, and keratinized cells in red to deep red. Hematoxylin staining is also generally used. Hematoxylin stains cell nuclei, calcified parts, cartilage tissues, bacteria, and mucus in blue to pale blue. The method of simultaneously performing eosin staining and hematoxylin staining is known as hematoxylin-eosin staining (HE stain).

The morphological staining can be performed according to a common method. For example, in the HE staining, the tissue sample is immersed in Mayer's Hematoxylin solution for hematoxylin staining, washed with running water, and then immersed in eosin solution for eosin staining. Conditions in the morphological staining, such as temperature and immersing time during which the tissue sample is immersed in the staining solution, can be appropriately adjusted according to a common method.

(2.3) Fluorescent Staining

Fluorescent staining is for staining the target substance with phosphor integrated dots so as to enable fluorescent observation. In the fluorescent staining, immunohistochemical staining is performed. In the immunohistochemical staining, an immunostainer solution is placed on the tissue section so that the solution reacts with the target substance. The immunostainer solution to be used in the immunohistochemical staining can be prepared before the fluorescent staining.

The fluorescent staining may be performed before or after the morphological staining.

(2.3.1) Target Substance

The target substance is a target of immunohistochemical staining with a fluorescent label so that the target substance is detected or quantified mainly in the pathological perspective. Specific examples of the target substance include biological substances, such as proteins (antigens) and nucleic acids present in the tissue section. The examples further include an antibody or nucleic acid contained in a pharmaceutical product that is given to a living body (e.g., antibody drug and nucleic acid drug). In this embodiment, any of the following biological substances is stained as the target substance.

As for protein, a protein that is expressed in immune cells and that can be used as a biomarker is usable. Examples of such a protein include PD-1, CTLA-4, TIM3, Foxp3, CD3, CD4, CD8, CD25, CD27, CD28, CD70, CD40, CD40L, CD80, CD86, CD160, CD57, CD226, CD112, CD155, OX40 (CD134), OX40L (CD252), ICOS (CD278), ICOSL (CD275), 4-1BB (CD137), 4-1BBL (CD137L), 2B4 (CD244), GITR (CD357), B7-H3 (CD276), LAG-3 (CD223), BTLA (CD272), HVEM (CD270), GITRL, Galectin-9, B7-H4, B7-H5, PD-L2, KLRG-1, E-Cadherin, N-Cadherin, R-Cadherin, IDO, TDO, CSF-1R, HDAC, CXCR4, FLT-3, or TIGIT, but are not limited to these.

Examples of a nucleic acid include DNA-related substances or RNA-related substances, such as mRNA, tRNA, rRNA, miRNA, or non-coding RNA.

Examples of a pharmaceutical product containing an antibody include: drugs containing an antibody as active ingredients; drugs that contain anticancer agents, antiviral agents, or antibiotics as active ingredients and that further contain an antibody that recognizes cancer cell-specific proteins as a delivery means to cancer cells; and drugs that contain an antibody that targets a factor of a signal transduction pathway related a factor (protein) targeted by an active ingredient. It is preferable that the antibody contained in these drugs be an antibody that specifically recognizes a cancer growth regulator, a metastasis regulator, a cancer cell-specific protein, or the like. Such and antibody may be a monoclonal antibody or a polyclonal antibody. The class and subclass of the antibody are not particularly specified. Examples of the class include IgA, IgG, IgE, IgD, and IgM. Examples of the subclass include IgG1, IgG2, IgG3, IgG4, IgA1, and IgA2. The term "antibody" in this description refers not only to a full-length antibody but also antibody fragments (e.g., Fab, F (ab)'2, Fv, and scFv), a chimeric antibody (e.g., humanized antibody), and derivatives (e.g., multifunctional antibody).

A nucleic acid-containing pharmaceutical product is not limited to a specific product as long as it contains nucleic acids as DNA or RNA, or artificial nucleic acids such as PNA. Preferred examples of such a product include decoy, antisense, siRNA, miRNA, ribozyme, aptamer, and plasmid DNA.

(2.3.2) Phosphor Integrated Dots

A phosphor integrated dot (PID) is a nano-sized particle that fluoresces when irradiated with excitation light and that can emit fluorescence at sufficient intensity to illuminate each molecule of the target substance as a bright spot.

The PID is a nano-sized particle having a base particle made of organic or inorganic substance. The base particle contains multiple fluorescent substances (e.g., fluorescent organic dye or quantum dots to be described later) and/or has the multiple fluorescent substances adhering to the surface of the base particle. Fluorescent dye-integrated dots, quantum dot-integrated dots, or the like are used.

It is preferable that the base particle and the fluorescent substance of the PID have substituents/parts having opposite electric charges and electrostatically interact with each other.

(2.3.2.1) Fluorescent Substance

The fluorescent substance used in the staining reagent for obtaining a fluorescent image may be a fluorescent organic dye and/or quantum dots (semiconductor particles). It is preferable that the fluorescent substance emit light having a wavelength in the range of 400 to 1000 nm (visible light to near-infrared rays) when excited by light having a wavelength in the range of 200 to 700 nm (ultraviolet rays to near-infrared rays).

Examples of the fluorescent organic dye include: fluorescein dye molecules, rhodamine dye molecules, Alexa Fluor (made by Invitrogen) dye molecules, BODIPY (made by Invitrogen) dye molecules, cascade dye molecules, coumarin dye molecules, eodin dye molecules, NBD dye molecules, pyrene dye molecules, Texas Red dye molecules, and cyanine dye molecules.

More specifically, the fluorescent organic dye may be: 5-carboxy-fluorescein, 6-carboxy-fluorescein, 5,6-dicarboxy-fluorescein, 6-carboxy-2', 4, 4', 5', 7, 7'-hexachlorofluorescein, 6-Carboxy-2', 4, 7, 7'-tetrachlorofluorescein, 6-carboxy-4', 5'-dichloro-2', 7'-dimethoxyfluorescein, naphthofluorescein, 5-carboxy-rhodamine, 6-carboxy-rhodamine, 5,6-dicarboxy-rhodamine, rhodamine 6G, tetramethyl rhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (these are made by Invitrogen), methoxycumarin, eodin, NBD, pyrene, Cy5, Cy5.5, or Cy7. One kind of dye may be used, or different kinds of dyes may be combined.

As the quantum dot, any quantum dot that contains a group II-VI compound, a group III-V compound, or a group IV element can be used. The quantum dots containing these components are called group II-VI quantum dot, group III-V quantum dot, group III-V quantum dot, and Group IV quantum dot, respectively. One kind of quantum dot may be used, or different kinds of quantum dots may be combined.

Specific examples of the component include CdSe, CdS, CdTe, ZnSe, ZnS, ZnTe, InP, InN, InAs, InGaP, GaP, GaAs, Si, and Ge, but the component is no limited to these.

A quantum dot that includes any of the above quantum dots as a core and a shell thereon can also be used. In this description, a quantum dot with a shell is expressed as CdSe/ZnS, where the core is CdSe and the shell is ZnS. Examples of such quantum dots include: CdSe/ZnS, CdS/ZnS, InP/ZnS, InGaP/ZnS, Si/SiO2, Si/ZnS, Ge/GeO2, Ge/ZnS. However, the quantum dot is not limited to these.

A quantum dot the surface of which is treated with an organic polymer or the like may be used as needed. Examples of such surface-treated quantum dots include: CdSe/ZnS having a surface carboxy group (made by Invitrogen) and CdSe/ZnS having a surface amino group (made by Invitrogen).

The fluorescent substance integrated in the PID can be a "long afterglow phosphor" that includes Y2O3, Zn2SiO4, or the like as a base and Mn2+, Eu3+, or the like as an activator, as well as the above-described fluorescent organic dye and quantum dots.

(2.3.2.2) Base

Examples of the base include organic substances, such as: resins generally classified as thermosetting resins, such as melamine resin, urea resin, aniline resin, guanamine resin, phenol resin, xylene resin, and furan resin; resins generally classified as thermoplastic resins, such as styrene resin, acrylic resin, acrylonitrile resin, AS resin (acrylonitrile-styrene copolymers), and ASA resin (acrylonitrile-styrene-methyl acrylate copolymers); other resins, such as polylactic acid; and polysaccharides.

Examples of the base further include inorganic substances, such as silica and glass.

(2.3.2.3) Quantum Dot-Integrated Dots

A quantum dot-integrated dot has a structure in which the above-described quantum dots are contained in the base and/or adhered to the surface of the base.

When the quantum dots are contained in the base, the quantum dots may or may not be chemically bonded to the base, as long as they are dispersed in the base.

(2.3.2.4) Fluorescent Dye-Integrated Dots

The fluorescent dye-integrated dot has a structure in which the fluorescent organic dye is contained in the base and/or adhered to the surface of the base.

When the fluorescent organic dye is contained in the base, the fluorescent organic dye may or may not be chemically bonded to the base, as long as the fluorescent organic dye is dispersed in the base.

(2.3.2.5) Preparation of Phosphor Integrated Dots

The phosphor integrated dots can be prepared according to a common method.

More specifically, for example, fluorescent substance-containing silica nanoparticles that contain silica as a base and fluorescent substances in the base can be prepared by: adding a drop of a solution in which fluorescent substances (e.g., quantum dots or fluorescent organic dye, and a silica precursor (e.g., tetraethoxysilane) are dissolved to a solution in which ethanol and ammonia are dissolved; and hydrolyzing the silica precursor.

As another example, phosphor integrated resin dots that contain resin as a base and fluorescent substances adhered to the surface of the resin or contained in the resin particles can be prepared by: firstly preparing a solution of the resin or a dispersion liquid of fine resin particles; and adding fluorescent substances (e.g., the quantum dots and/or fluorescent organic dye) to the solution/dispersion liquid and mixing them. The phosphor integrated resin dots can also be prepared by adding fluorescent substances to the solution of resin material and causing the polymerization reaction.

For example, when thermosetting resin (e.g., melamine resin) is used as the base resin, fluorescent dye integrated-resin dots can be prepared by: heating a reaction mixture that contains material of the base resin (monomer, oligomer or prepolymer, such as methylol melamine that is a condensation product of melamine and formaldehyde), fluorescent organic dye, and preferably a surface-active agent and polymerization promoter (e.g., acid); and causing polymerization reaction by the emulsion polymerization method. When a thermoplastic resin (e.g., tyrene-based copolymer) is used as the base resin, fluorescent dye integrated-resin dots can be prepared by: heating a reaction mixture containing material of the base resin, fluorescent organic dye, and a polymerization initiator (e.g., benzoyl peroxide, azobisisobutyronitrile); and causing polymerization reaction by the radical polymerization method or the ionic polymerization method. As a material monomer of the resin, a monomer may be used that has been bonded with the organic fluorescent dye by a covalent bond or the like.

(2.3.2.6) Average Particle Diameter

The average particle diameter of the phosphor integrated dots used in this embodiment is not limited to a specific size. The dots having a large particle diameter have less access to antigen. The dots having a small particle diameter have a lower brightness value, and their signals may be buried in background noise (camera noise or auto fluorescence of cells). It is therefore preferable that the particle diameter be around 20 to 500 nm. A coefficient of variation that indicates variation in particle diameter (=(standard deviation/average value)×100%) is not limited to a particular value but can be equal to or less than 20%. It is preferable that the coefficient be between 5 to 15%.

The average particle diameter is obtained by: capturing an electron microscope image(s) of a sufficient number of phosphor integrated dots using a scanning electron microscope (SEM); measuring the cross section of the dots; and obtaining the diameter of a circle having the measured area of each dot as the particle diameter of the dot. In the present invention, the average particle diameter is an arithmetic mean of particle diameters of 1,000 dots. The coefficient of variation is calculated from the distribution of particle diameters of 1,000 dots.

(2.3.3) Antibody

As the primary antibody, such an antibody (IgG) can be used that specifically recognizes a protein being a target substance as an antigen and bonds with the protein.

The primary antibody may not be a natural full-length antibody but may be an antibody fragment or derivative, as long as the primary antibody is capable of specifically recognizing and bonding with a specific biological substance (antigen).

As the secondary antibody, such an antibody (IgG) can be used that specifically recognizes the primary antibody as an antigen and bonds with the primary antibody.

The primary and secondary antibodies may be a polyclonal antibody. It is, however, preferable that the primary and secondary antibodies be a monoclonal antibody in terms of quantitative stability. The animal (immune animal) that produces antibodies is not limited to a specific animal and may be selected from, for example, mice, rats, guinea pigs, rabbits, goats, and sheep, as in the known art.

(2.3.4) Immuno Stainer

An immunostainer is produced by dispersing a labeled antibody in an appropriate medium. In the labeled antibody, a labeling substance is directly or indirectly bonded with an antibody capable of being directly or indirectly bonded with a target substance.

To improve efficiency of fluorescent labeling and prevent deterioration of fluorescence with the passage of time as much as possible, it is preferable that the immunostainer be a complex in which the primary antibody and the phosphor integrated dots are indirectly bonded with each other (i.e., bonded not by a covalent bond but by a bond utilizing antigen-antibody reaction or avidin-biotin reaction). The immunostainer is not limited to this, though.

Following is an example of the immunostainer in which an antibody and fluorescent nanoparticles are indirectly bonded.

[primary antibody for target biological substance] . . . [antibody for primary antibody (secondary antibody)]~[fluorescent nanoparticle (phosphor integrated dot)] Herein, " . . . " indicates a bond by an antigen-antibody reaction. "~" indicates a bond the type of which is not specifically limited. "~" may be, for example, a covalent bond, ionic bond, hydrogen bond, coordination bond, physical adsorption, or chemisorption. The bond indicated by "~" may be mediated by a linker molecule if necessary.

A conjugate of the secondary antibody ~phosphor integrated dot can be prepared with a silane coupling agent, for example. The silane coupling agent is a widely used compound for bonding inorganic material and organic material. The silane coupling agent is a compound having (i) an alkoxysilyl group that provides a silanol group with hydrolysis in one end of the molecule and (ii) a functional group, such as carboxy group, amino group, epoxy group, aldehyde group, or the like in the other end. The silane coupling agent is bonded with inorganic substances via an oxygen atom of the silanol group. Specific examples of the silane coupling agent include mercaptopropyltriethoxysilane, glycidoxypropyltriethoxysilane, aminopropyltriethoxysilane, and a silane coupling agent having a polyethylene glycol chain (e.g., PEG-silaneno. SIM6492.7 made by Gelest). Two or more kinds of silane coupling agents may be used together.

The reaction between the phosphor integrated dots and the silane coupling agent may be caused by a known method. For example, silica nanoparticles that contain obtained fluorescent substances are dispersed in pure water and added with aminopropyl triethoxysilane to let the reaction occur for 12 hours at room temperature. After the reaction, the materials are subject to centrifugal separation or filtration to obtain silica particles that contain fluorescent substances and the surfaces of which are modified with the aminopropyl group. Next, a reaction is caused between the amino groups and the carboxy groups in the antibody, so that the antibody is bonded via an amide bond with silica nanoparticles containing fluorescent substances. A condensing agent, such as EDC (1-Ethyl-3-[3-Dimethylaminopropyl] carbodiimide Hydrochloride: made by Pierce), may be used as necessary.

Further, a linker compound may be used that has (i) a portion capable of being directly bonded with silica nanoparticles that contain organic molecule-modified fluorescent substances and (ii) a portion capable of being bonded with a molecular target substance. More specifically, sulfo-SMCC (Sulfosuccinimidyl-4-[N-maleimidomethyl] cyclohexane-1-carboxylate, made by Pierce) may be used. Sulfo-SMCC has both (i) a portion that selectively reacts with an amino group and (ii) a portion that selectively reacts with a mercapto group. With sulfo-SMCC, silica nanoparticles that contain fluorescent substances bonded with the antibody are obtained by bonding amino groups of silica nanoparticles containing fluorescent substances modified with aminopropyltriethoxysilane with mercapto groups in the antibody.

In bonding polystyrene particles containing fluorescent substances with biological substance-recognizing portions (portions where biological substances can be specifically recognized, such as biotin, avidin and an antibody), the same method can be applied regardless of whether the fluorescent substances are fluorescent organic dye or quantum dots. More specifically, phosphor integrated polystyrene dots having functional groups can be obtained by impregnating polystyrene nanoparticles having functional groups (e.g., amino groups) with quantum dots or fluorescent organic dye. Then, by using EDC or sulfo-SMCC, the phosphor integrated polystyrene dots bonded with the antibody can be obtained.

Another example of the immunostainer in which the antibody and fluorescent nanoparticles are indirectly bonded is a complex of three monocules combined as follows.

[Primary antibody for target substance] . . . [antibody for primary antibody (secondary antibody)]–[biotin]/[avidin]–[fluorescent substance (phosphor integrated dot)]

Herein, the notation " . . . " indicates a bond by an antigen-antibody reaction. The hyphen "—" indicates a bond by a covalent bond that may be mediated with a linker molecule, if necessary. The slash "/" indicates a bond by an avidin-biotin reaction.

A conjugate of the secondary antibody-biotin (biotin-modified secondary antibody) can be prepared according to a known method that can bond a desired antibody (protein) with biotin. For example, commercial biotin labeling reagents (kits) available on the market may be used. A biotin-modified secondary antibody in which a desired antibody and biotin are bonded and that is available on the market may be used.

A conjugate of the phosphor integrated dot-avidin (avidin-modified fluorescent substance) can also be prepared according to a known method that can bond a fluorescent substance with avidin. For example, avidin labeling reagents (kits) available on the market may be used. In the case, avidin may be an improved type of avidin, such as streptavidin or neutravidin that can be bonded stronger with biotin than avidin.

A detailed example of a method for preparing a conjugate of the phosphor integrated dot-avidin is as follows.

When the base of the phosphor integrated dot is resin, a functional group in the resin can be bonded with a functional group of avidin (protein) via a linker molecule, such as PEG that has functional groups at both ends of its molecule, if necessary. For example, when the base is a melamine resin, a functional group, such as an amino group, can be used. When the base is an acrylic resin, a styrene resin or the like, a monomer having a functional group (e.g., epoxy group) on a side chain can be copolymerized, so that the functional group itself or a functional group converted from the original functional group (e.g., amino group generated by reaction with ammonia water) can be used. Further, these functional groups can be utilized to introduce other functional groups.

When the base of the phosphor integrated dot is silica, a desired functional group can be introduced by surface modification with a silane coupling agent. For example, an amino group can be introduced by using aminopropyltrimethoxysilane.

For avidin, a thiol group can be introduced to avidin by causing a reaction between an amino group of avidin and N-succinimidyl S-acetylthioacetate (SATA), for example. The phosphor integrated dot having an amino group and the avidin to which the thiol group is introduced can be connected with a cross-linker reagent. The cross-linker reagent has, at both ends of a polyethylene glycol (PEG) chain, (i) a N-hydroxysuccinimide (NHS) ester that reacts with an amino group and (ii) a maleimide group that reacts with a thiol group.

The conditions under which fluorescent staining is performed (i.e., temperature and immersing time in immersing the tissue sample in the immunostainer solution) can be appropriately adjusted so as to obtain an appropriate signal, according to a known immunohistochemical staining method.

fluorescent staining can be performed at room temperature, although temperature is not specifically limited. Preferably, the immersing time is between 30 minutes to 24 hours.

Before performing the above-described treatment, it is preferable that drops of a known blocking agent, such as PBS containing BSA, and/or a surface-active agent, such as Tween 20, be added.

For example, when the immunostainer is a complex of [primary antibody (probe)] . . . [secondary antibody]–[biotin]/[avidin]–[fluorescent nanoparticle (e.g., phosphor integrated dot)], firstly the tissue sample is immersed in the solution of the primary antibody (primary reaction treatment). Secondly, the tissue sample is immersed in the solution of the secondary antibody-biotin conjugate (secondary reaction treatment). Lastly, the tissue section, which is the tissue sample, is immersed in a diluted solution for fluorescent nanoparticles in which avidin-fluorescent nanoparticles are dispersed (fluorescence labeling treatment).

(2.4) Aftertreatment of Sample

It is preferable that the tissue sample after the morphological staining and the fluorescent staining be subjected to treatments, such as fixation and dehydration, permeation, and encapsulation, so as to be suitable for observation.

For fixation and dehydration treatment, the tissue sample may be immersed in a fixation treatment solution (cross-linking agent, such as formalin, paraformaldehyde, glutaraldehyde, acetone, ethanol, and methanol). For the permeation treatment, the tissue sample after the fixation and dehydration treatment may be immersed in a permeation solution (e.g., xylene). For the encapsulation treatment, the tissue sample after the permeation treatment may be immersed in a encapsulation liquid.

The conditions under which these treatments are performed (e.g., temperature and immersing time in immersing the tissue sample in specific treatment solutions) can be appropriately adjusted so as to obtain an appropriate signal, according to a known immunohistochemical staining method.

(3) Image Obtaining

In image obtaining, the bright field unit is set in the microscope image-obtaining device 1A, the magnification is set to a desired magnification, and a bright-field image of the whole tissue sample stained in the morphological staining is observed and imaged.

Next, the fluorescence unit is set in the microscope image-obtaining device 1A, the tissue sample is irradiated with excitation light corresponding to each fluorescent substance that fluorescently labels the target substance used in the fluorescence staining A fluorescent image of the whole tissue sample is observed and captured with fluorescence emitted from the fluorescent substances.

(4) Score Creating

In score creating, firstly multiple kinds of information on regions, structures, and cell types in the bright-field image are obtained, and then a morphological score(s) is calculated by combining and scoring these multiple kinds of information.

A software usable for image processing and scoring is, for example, "ImageJ" (open source). Such an image processing software can semi-automatically and quickly perform: a process for identifying regions, structures, and cell types based on the shapes of respective cells, regions formed by gathering cells, and structures; and a process for calculating scores based on information on the number and areas of regions, structures, and cell types, for example.

Next, information on the presence of target substances in the fluorescent image is obtained and scored to obtain a biological substance score. The information on the presence of target substances is, for example, information on the amount of target substances (e.g., protein, nucleic acid, and antibody contained in a pharmaceutical product) present in one cell and information on positions of target substances in cells. More specifically, the information provision device 2A: performs image processing on the fluorescent image that captures the target substances; extracts fluorescent labeling signals, such as fluorescent bright spots that correspond to the target substances; identify the coordinates of the respective bright spots or count the bright spots; and quantify the abundance and intracellular localization of the target substances, thereby scoring the fluorescent image. When multiple types of target substances are stained, the biological substance score can be calculated for each type of target substance.

The software, such as the above-mentioned "ImageJ" (open source), can also be used for image processing and expression analysis. Accordingly, the process of extracting the bright spots having certain wavelengths (colors) and counting the bright spots having a certain level of brightness or greater, for example can be performed semi-automatically and quickly.

Lastly, the morphological score calculated based on the bright-field image and the biological substance score calculated based on the fluorescent image are added up to create a final analysis score.

(5) Region Visualization

The pathological diagnosis support system 100 in this embodiment can also perform fluorescent staining as needed so as to distinguish between tumor regions and interstitial regions. For example, substances that are abundantly present in interstitial regions are fluorescently labeled and observed. This allows the user to confirm the boundaries between the interstitial regions where fluorescence is observed and the tumor regions where no fluorescence or weak fluorescence tendency is observed by fluorescence observation. The pathological diagnosis support system 100 thus can support discrimination between tumor regions an interstitial regions in the bright-field images.

More specifically, the following staining is applicable.

(5.1) Fluorescent Staining of Cytokines

Fluorescent labeling of cytokines present in the interstitial region enables clear discrimination between the tumor region and the interstitial region by fluorescence observation. Since the interstitial region has a large amount of cytokines as compared with the tumor region, difference in fluorescence brightness allows the user to visually confirm boundaries between the interstitial region and the tumor region.

In the fluorescent staining, the tissue sample is stained with an immuno stainer containing an antibody (IgG) that specifically recognizes and bonds with a cytokine as an antigen and that is labeled with fluorescent substances. The fluorescent substance used in fluorescent labeling is not limited to phosphor integrated dots. A single kind of fluorescent dye sufficiently enables discrimination between the tumor region and the interstitial region.

More specifically, staining can be performed according to the process described in (2.3) fluorescent staining. Fluorescent staining of cytokines can be performed simultaneously with fluorescent staining of the target substance in the above (2.3) fluorescent staining. It is preferable, however, that the fluorescence wavelength of a fluorescent substance for cytokines be different from the fluorescence wavelength of the phosphor integrated dots for labeling the target substance.

Examples of cytokines include IL-1, IL-2, IL-4, IL-6, IL-10, IL-12, IL-18, IFN-α, IFN-γ, IFN-γ, TNF, and TGF-β.

(5.2) Fluorescent Staining of Proteins in Immune Cells

A protein in an immune cell herein refers to a protein that is specifically expressed in an immune cell. Fluorescent labeling of the protein enables clear discrimination between the tumor region and the interstitial region by fluorescent observation. More specifically, the boundaries between the tumor region and the interstitial region are visually recognizable based on difference in brightness, since the fluorescent brightness of immune cells in the interstitial region is significantly greater than the fluorescent brightness of immune cells in the tumor region. When fluorescence staining is performed for a protein that is highly expressed in the interstitial region in the above "(2.3) fluorescent staining", the process of (5.2) can be substituted by fluorescence observation of the target substance. When fluorescence staining is not performed for the highly-expressed protein in (2.3), fluorescent staining of the protein in (5.2) is effective. Examples of the protein are described below.

In (5.2), an antibody (IgG) that specifically recognizes and binds to a protein as an antigen in immune cells is used. The tissue sample is stained with an immunostainer that contains the antibody labeled with fluorescent substances. The fluorescent substance used for fluorescent labeling is not limited to phosphor integrated dots. A single kind of fluorescent dye sufficiently enables discrimination between the tumor region and the interstitial region. Staining in (5.2) can be performed in the same process as (2.3) fluorescent staining Examples of proteins in immune cells include PD-1, CTLA-4, TIM3, Foxp3, CD3, CD4, CD8, CD25, CD27, CD28, CD70, CD40, CD40L, CD80, CD86, CD160, CD57, CD226, CD112, CD155, OX40 (CD134), OX40L (CD252), ICOS (CD278), ICOSL (CD275), 4-1BB (CD137), 4-1BBL (CD137L), 2B4 (CD244), GITR (CD357), B7-H3 (CD276), LAG-3 (CD223), BTLA (CD272), HVEM (CD270), GITRL, Galectin-9, B7-H4, B7-H5, PD-L2, KLRG-1, E-Cadherin, N-Cadherin, R-Cadherin, IDO, TDO, CSF-1R, HDAC, CXCR4, FLT-3, and TIGIT.

<Operation of Pathological Diagnosis Support System 100>

Hereinafter, operation of the pathological diagnosis support system 100 for obtaining and analyzing the above-described fluorescent image and the bright-field image is described. Herein, as an example case, a protein is selected as a target substance from proteins expressed in immune cells of a tissue samples an observation target; and the tissue sample is stained with a staining reagent that contains phosphor integrated dots bonded with biological substance-recognizing portions that recognize the target substance.

First, the operator stains the tissue sample with two types of staining reagents. One staining reagent is an HE staining reagent. The other staining reagent contains, as a fluorescent labeling material, phosphor integrated dots bonded with biological substance-recognizing portions that recognize the target substance.

Next, the microscope image-obtaining device 1A obtains a bright-field image and a fluorescent image in accordance with (a1) to (a5).

(a1) The operator places the tissue sample stained with the HE staining reagent and the staining reagent containing phosphor integrated dots on a slide, and then places the slide on the slide fixing stage of the microscope image-obtaining device 1A.

(a2) Set the bright field unit in the microscope image-obtaining device 1A and adjust the imaging magnification and focus.

(a3) Image the whole tissue sample with the imaging unit to generate image data of a bright-field image, and send the image data to the information provision device 2A.

(a4) Replace the bright field unit with the fluorescent unit.

(a5) Image the whole tissue sample with the imaging unit without changing the imaging magnification and focus to generate image data of a fluorescent image, and send the image data to the information provision device 2A.

Next, the information provision device 2A performs image obtaining, score creating, and information presenting.

Figure 3:
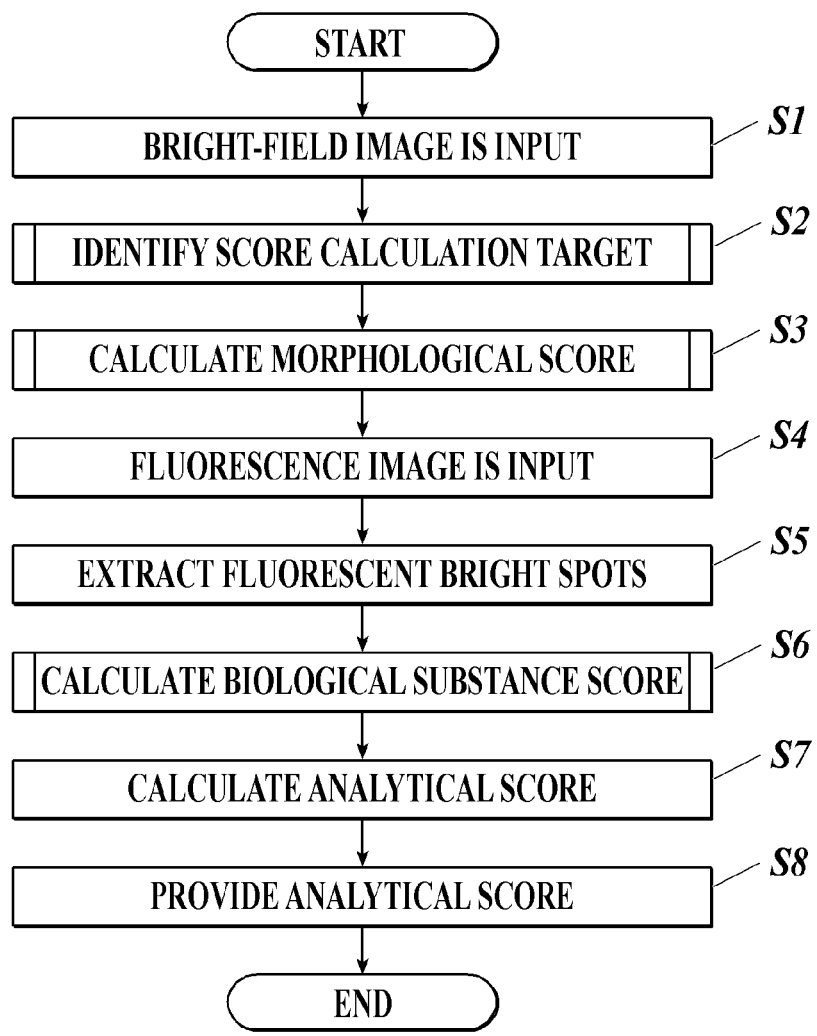
FIG. 3 is a flowchart of operations performed by the information provision device.

FIG. 3 shows a flowchart of the process performed by the information provision device 2A. The process shown in FIG. 3 is performed by the controller 21 in cooperation with the program stored in the storage 25.

First, when the bright-field image is input from the microscope image-obtaining device 1A via the communication I/F 24 under the control of the controller 21 (Step S1: image obtaining), the score calculation target is identified (Step S2).

Figure 4:
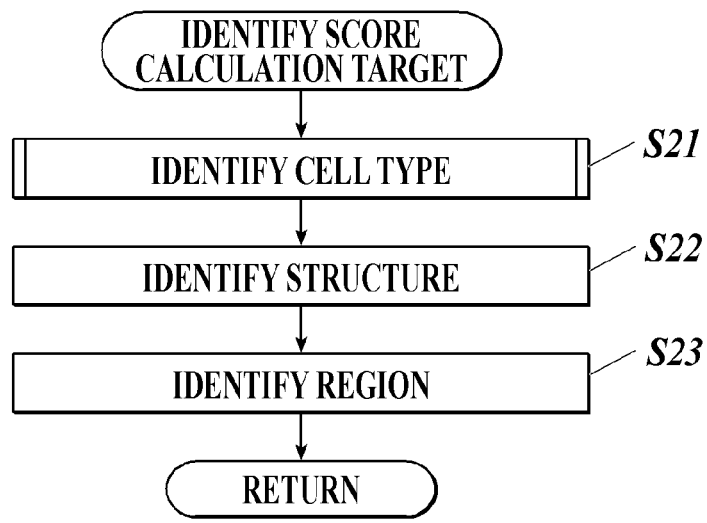
FIG. 4 is a flowchart of a process for identifying a score calculation target.

FIG. 4 shows a detailed flow in Step S2. The process in Step S2 is performed by the controller 21 in cooperation with the program stored in the storage 25.

In Step S2, firstly the cell type is identified (step S21).

Figure 5:
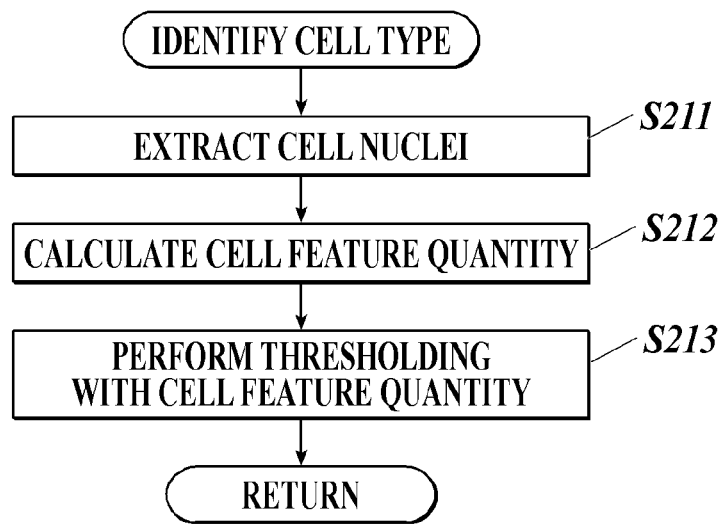
FIG. 5 is a flowchart of a process for identifying a cell type.

FIG. 5 shows a detailed flow in step S21. The process in step S21 is performed by the controller 21 in cooperation with the program stored in the storage 25.

In step S21, firstly cell nuclei are extracted (step S211).

More specifically, the bright-field image is converted into a monochrome image, and the monochrome image is subjected to thresholding with a predetermined threshold, so the values of respective pixels are binarized.

The monochrome image is further subjected to noise processing through closing processing and opening processing. After the noise processing, an image in which the cell nuclei have been extracted (cell nucleus image) is obtained.

The image after the noise processing is then subject to labeling. In the labeling, each of the extracted cell nuclei is labeled. In the labeling, the same label (number) is given to connected pixels so as to distinguish objects in the image. Through the labeling, each cell nucleus in the image after the noise processing can be distinguished and labeled.

Instead of cell nuclei, cells themselves may be extracted in step S211. In the case, after the noise processing, an image in which cells have been extracted is obtained, and each of the cells is labeled through the labeling.

Next, cell feature quantities are calculated (step S212).

More specifically, cell feature quantities are calculated for all of the cell nuclei extracted in the cell nucleus image in Step S211. The cell feature quantities include: the cell nucleus area A, the average concentration of the cell nucleus B, pixel brightness variation in the cell nucleus (value of a) C, the circularity of the cell nucleus D, and oblateness of the cell nucleus E.

The cell nucleus area A for a cell nucleus is determined by: calculating beforehand the area of a pixel on the basis of a reference length for a cell nucleus image; and multiplying the area of a pixel with the number of pixels in the cell nucleus extracted in step S211.

The average concentration of the cell nucleus B is determined by obtaining brightness signal values converted to gray scales of the respective pixels in the cell nucleus and calculating the average of the values. The pixel brightness variation in the cell nucleus C is determined by the standard deviation of the brightness signal value of each pixel in the cell nucleus.

The circularity D and oblateness E of each cell nucleus extracted in Step S211 are determined by using the following formulas (d), (e) and certain values of the cell nucleus. The values are obtained from the cell nucleus image.

$$(\text{Circularity } D) = 4\pi S/L^2 \quad (d)$$

$$(\text{Oblateness } E) = (a-b)/a \quad (e)$$

In the formula (d), "S" represents the cell area (cell nucleus area A), and "L" represents the outer circumferential length of the cell nucleus. In the formula (e), "a" represents a semi-major axis, and "b" represents a semi-minor axis.

Next, thresholding is performed with the calculated cell feature quantities (step S213). For example, thresholds for distinguishing between tumor cells and normal cells are set for the respective cell feature quantities A to E, and thresholding is performed for all of the cell nuclei in the cell nucleus image. Accordingly, the cell is identified as a tumor cell or a normal cell. In addition, thresholding may be performed to identify cell types, such as immune cells, inflammatory cells, fibroblasts, and endothelial cells, in the interstitial region. Thresholds can be set as desired for other cell types to be identified so as to identify various cell types.

The elements of the cell feature quantities A to E are examples. Elements of the cell feature quantities may be different from the above-described elements. For example, in comparing tumor cells with normal cells in pathological diagnosis, sizes and shapes of cells, positions, size and change in shape of cell nuclei, images of nuclear division, cytoplasmic color, presence/absence of mucus production, and ratio of cell nucleus area to cytoplasm area are observed. These items that are observed in actual pathological diagnosis may be extracted as cell feature quantities for identification of cell types.

Next, structures, such as blood vessels, lymphatic vessels, and secreting glands, are identified (Step S22).

In Step S22, structures that are formed of a certain amount of gathering cells are extracted from the cell nucleus image, for example. Next, feature quantities, such as area, average brightness, brightness variation, oblateness, and circularity of a structure, are calculated from each of the extracted structures. On the basis of the feature quantities, blood vessels, lymphatic vessels, secreting glands, and so forth are identified.

Next, regions are identified (Step S23).

In identifying regions, a tumor region constituted of a certain amount of gathering tumor cells and an interstitial region constituted of a certain amount of gathering interstitial cells are identified.

In Step S23, when a gathering of cells (cell nuclei) identified as tumor cells in step S21 occupies a predetermined area or more in the cell nucleus image, the gathering of tumor cells can be identified as a tumor region, for example. Similarly, when a gathering of cells (cell nuclei) identified as interstitial cells in step S21 occupies a predetermined area or more, the gathering of interstitial cells can be identified as an interstitial region.

After the process of step S23, identification of the score calculation target ends.

Basically, the process of identifying the score calculation target in the above steps S21 to S23 is automatically performed by the controller 21 in cooperation with the program stored in the storage 25. The process may be accompanied with assistance by a user (e.g., pathologist).

Examples of the assistance by the user include selecting a specific region in the region identification process in Step S21. In step S21, the user may select the specific region in the bright-field image displayed on the display 23 of the information provision device 2A by enclosing the region in a polygon or free form curves using the operation receiver 22, and defines the selected region as "tumor region", "interstitial region", and so forth. The examples further include the user's validation of the result of region identification in the bright-field image by observing fluorescence in the fluorescent image.

The examples further include the user's operation of selecting and defining structures/cell types in the bright-field image in structure identification in step S22 and cell type identification in step S23.

The examples further include the user's assistance in thresholding with the cell feature quantities in Step S233. For example, the user may adjust thresholds of respective cell feature quantities stepwise in the program stored in the storage 25 and visually confirm the identified cell types.

The identification of the score calculation target in steps S21 to S23 may be performed with methods other than the above method. More specifically, the identification may be automatically performed using the image recognition technique trained with machine learning. For example, a technique, such as a neural network, random forest, or SVM (Support Vector Machine) may be trained to learn regions, structures, and cell types that appear in bright-field images, so that these items are automatically identified in input bright-field images.

Next, a morphological score(s) is calculated (step S3: score creating).

Figure 6:
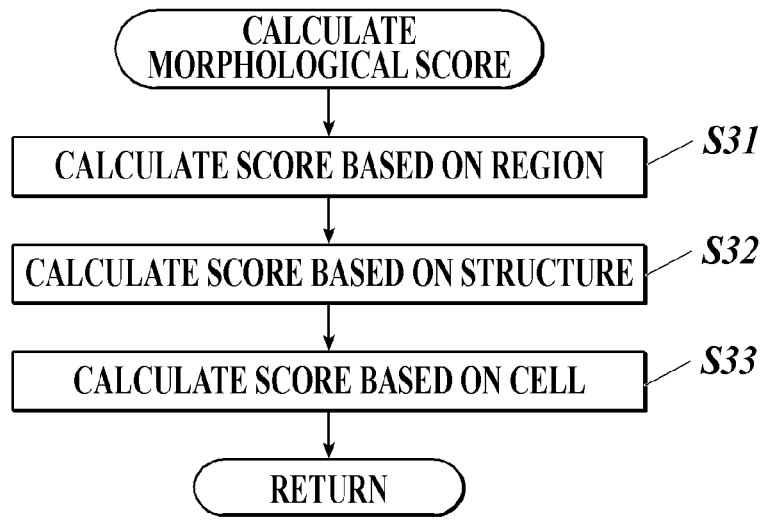
FIG. 6 is a flowchart of a process for calculating a morphological score.

FIG. 6 shows a detailed flow of step S3. The process in step S24 is performed by the controller 21 in cooperation with the program stored in the storage 25.

In step S3, firstly a score(s) based on regions is calculated (step S31).

The score based on regions is a score given to information obtained from various regions, such as tumor regions and interstitial regions present in the tissue section. The area of a tumor region is associated with the degree of malignancy of cancer. Therefore, for example, scoring the ratio of the tumor region area to the whole area of the imaged tissue sample, the ratio of the tumor and interstitial region area to the whole area, and the ratio of the interstitial region area to the tumor region area may be useful.

Next, a score(s) based on structures is calculated (step S32).

The score based on structures is a score given to information obtained from various structures, such as blood vessels, lymphatic vessels, and secretory tubules. The concentration of blood vessels is known as an evaluation index of the malignancy of cancer. Therefore, for example, scoring the presence/absence, the concentration, and the number of structures associated with the degree of malignancy of cancer in the tissue section may be useful.

Next, a score(s) based on cell types is calculated (step S33).

A score based on cell types is a score given to information obtained from cell types present in the tissue section, such as tumor cells and interstitial cells. For example, the number of cancer cells and the number of normal cells present in the tissue section may be scored. Further, various kinds of information observed in pathological diagnosis may be scored. For example, the concentration of cancer cells in the tissue section, the distance between different cells (e.g., distance between cancer cells in the tumor region and immune cells in the interstitial region) and the distance between specific cell types and structures (e.g., distance between cancer cells in the tumor region and blood vessels in the interstitial region) may be scored.

After Step S33, calculation of the morphological score ends, and the controller 21 returns to the process in FIG. 3.

In steps S31 to S33, each score may be weighted based on the purpose of observation, or scores may be subtotaled at a certain phase and the subtotal may be weighted. However, it is preferable that calculation of scores based on regions, structures, and cell types be performed in the order of steps S31 to S33. The order of (i) evaluating areas and so forth of tumor regions present in the tissue section, (ii) evaluating structures (e.g., blood vessels) present in the tissue section, and (iii) evaluating the number, positions, and so forth of tumor cells is the same as the order when a pathologist actually observes a tissue sample and make diagnosis. With the process similar to diagnosis process in clinical fields, accuracy in support information can be improved.

The method of calculating the score based on regions, the score based on structures, and the score based on cell types is not limited to the above example method. Further, it is preferable that items to be observed in pathological diagnosis be scored.

When the fluorescent image is input from the microscope image-obtaining device 1A via the communication I/F 24 (Step S4: image obtaining), fluorescent bright spots are extracted from the fluorescent image (Step S5).

In step S5, firstly R components are extracted from the fluorescent image, and the fluorescent image in which the R components are extracted is subjected to Tophat conversion. In Tophat conversion, the input image is filtered with the minimum filter and the maximum filter in this order, and pixel values in the filtered image are subtracted from the corresponding pixel values of the original input image. The minimum filter replaces the value of a target pixel with the minimum value among the pixels around the target pixel (e.g., 3×3 pixels). The maximum filter replaces the value of a target pixel with the maximum value among the pixels around the target pixel (e.g., 3×3 pixels). Tophat conversion can extract protrusions in the tone profile (regions having higher brightness levels than the neighboring pixels). Accordingly, a fluorescent-bright-spot candidate image can be obtained. Next, noise is removed from the fluorescent-bright-spot candidate image. This yields an image in which fluorescent bright spots are extracted (fluorescent bright spot image). The fluorescent bright spot image is subject to labeling, so that the respective extracted fluorescent bright spots are labeled.

Next, a biological substance score is calculated (step S6 score creating).

Figure 7:
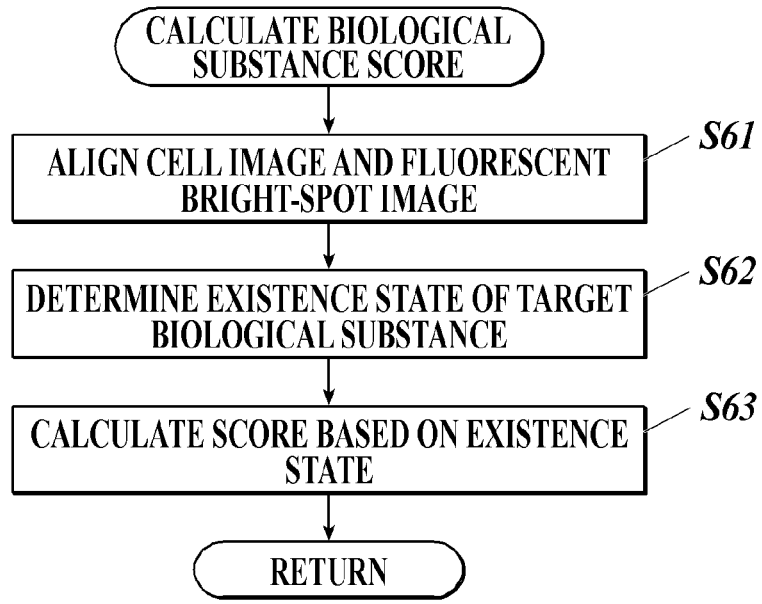
FIG. 7 is a flowchart of a process for calculating a biological substance score.

FIG. 7 shows a detailed flow of step S6. The process in step S6 is performed by the controller 21 in cooperation with the program stored in the storage 25.

In step S6, firstly the bright-field image and the fluorescent image are aligned based on information that is commonly detected in the bright-field image and the fluorescent image (step S61). The bright-field image used in the alignment is the cell nucleus image obtained in step S2. The fluorescent image used in the alignment is the fluorescent bright spot image obtained in step S5.

The information that is commonly detected in the bright-field image and the fluorescent image is the information that can be recognized in both the bright-field image and the fluorescent image. In this embodiment, the information is on eosin staining for staining the tissue section. On the basis of the information on eosin staining, image feature quantities are calculated. The image feature quantities include, for example, contrast information, edge information, and contour information that show the characteristics of the bright-field image and the fluorescent image.

The contrast information, edge information, and contour information of the bright-field image and the fluorescent image are extracted based on the information on eosin staining for the respective images. These kinds of information are compared between the bright-field image and the fluorescent image, and their common points are matched. Thus, the bright-field image and the fluorescent image are aligned.

Next, the existence state of the target substance in each cell is determined based on the bright-field image (cell nucleus image obtained in step S2) and the fluorescent image (fluorescent bright spot image obtained in step S5) that have been aligned (step S62).

More specifically, for example, fluorescent bright spots are counted in the portion corresponding to the cell identified in step S23, based on the bright-field image and the fluorescent image superposed on each other. In addition to or instead of the number of fluorescent bright spots, brightness values may be calculated for the respective bright spot portions to obtain a brightness integral value. The brightness integral value is the total of brightness values of all the bright spot portions in the fluorescent image.

Next, a score based on the existence state is calculated (step S63).

The score based on the existence state is a score calculated based on the abundance of the target substance per cell, intracellular localization of the target substance, and so forth. When multiple kinds of target substances are fluorescently stained, the treatments in steps S5 and S6 can be performed for each kind of target substance, so that a biological substance score is obtained for each kind of target substance.

After step S63, calculation of the biological substance score ends.

Next, an analysis score is calculated (step S7: score creating).

The analysis score is the total of the morphological score calculated in step S3 and the biological substance score calculated in step S6.

The morphological score and/or the biological substance score may be weighted as needed when being added up so that the user can obtain desired support information.

Next, the calculated analysis score is displayed on the display 23 (step S8: information presenting). This allows the user to check the analysis score presented as support information by the information provision device 2A. In step S8, the way of presenting the analysis score is not particularly limited. The analysis score may be presented just as itself as a numerical value. Alternatively, the analysis score may be presented on the bright-field image and the fluorescent image (the analysis score may be in the forms of morphological and biological substance scores). Displaying the analysis score in association with the images allows the user to easily view the correlation between the analysis score and the state of the tissue section, and therefore improves usability.

Thus, the processing by the information provision device 2A ends.

As described above, the information provision method in this embodiment creates the analysis score by obtaining, combining, and scoring multiple kinds of information from the digitized bright-field image of the tissue section, and presents the analysis score as support information to the user. Actual pathological diagnosis is performed based on multiple kinds of information obtained from the tissue section (e.g., the number of tumor cells and the number of immune cells), not on the basis of a single type of information (e.g., the number of tumor cells). The information provision method in this embodiment provides an analysis score that is created by comprehensively evaluating the tissue section based on multiple kinds of information, as in actual diagnosis. Such an analysis score serves as an accurate index in various judgments. The user can make pathological diagnosis based on the analysis score. The user can also compare the analysis score displayed on the information provision device 2A with his/her diagnosis made by observing the tissue section. Thus, the user can check the accuracy of his/her diagnosis.

Further, the information provision method in this embodiment digitally analyzes and evaluates images of the tissue section to provide objective information, as compared with subjective judgments by a pathologist. The information provision method can support various judgements in pathological diagnosis and improve accuracy of diagnoses.

Further, the microscope image is obtained with a virtual-microscope-slide creating device. This eliminates the need of making judgements based on a typical field of view, and enables judgments through observation of the whole tissue section.

Further, the analysis score can be created by combining information obtained from regions, structures, and cell types. The information provision method performs comprehensive evaluation based on the relationship of regions, structures, and cell types, as with a pathologist making actual pathological diagnosis. The information provision method thus can provide accurate support information.

Further, the analysis score is created based on information on the positional relationship of the regions, structures, and cell types (e.g., the distance between cancer cells in the tumor region and immune cells in the interstitial region, the distance between cancer cells and specific structures such as blood vessels). Thus, the information provision method can provide more reliable support information.

Further, scores are basically created based on regions, structures, and cell types, respectively. The items to be scored and to be weighted may be determined according to the purpose of observation. The information provision method thus can present information that the user requires as a score.

Further, a specific biological substance is stained with phosphor integrated dots so as to be fluorescently observable. Thus, the abundance of the biological substance is usable for creating the analysis score. Such an analysis score can serve as a new index in pathological diagnosis.

Further, by staining regions in different colors in the region staining, the boundaries between regions can be clearly and visually recognized. This improves credibility of the support information.

In the above embodiment, the target substance is fluorescently stained. This fluorescent staining can be omitted.

As described above, an object of the present invention is to support various judgments by a pathologist and so forth by automatically scoring information obtained from a pathological section and presenting the scores. This object can be fully achieved by creating a score based on combinations of multiple kinds of information obtained from the bright-field image of the section (information on regions, structures, and cell types), in a similar way as a pathologist evaluates the pathological section and makes judgements.

The present invention is different from Patent Literatures 1 and 2 in that fluorescent staining of the biological substance is not necessary and that the analysis score can be created only with the morphological staining. This can omit staining work and variation in slides through respective staining treatments.

Hereinafter, a specific example of calculating the analysis score is described with reference to FIG. 8.

Figure 8A:
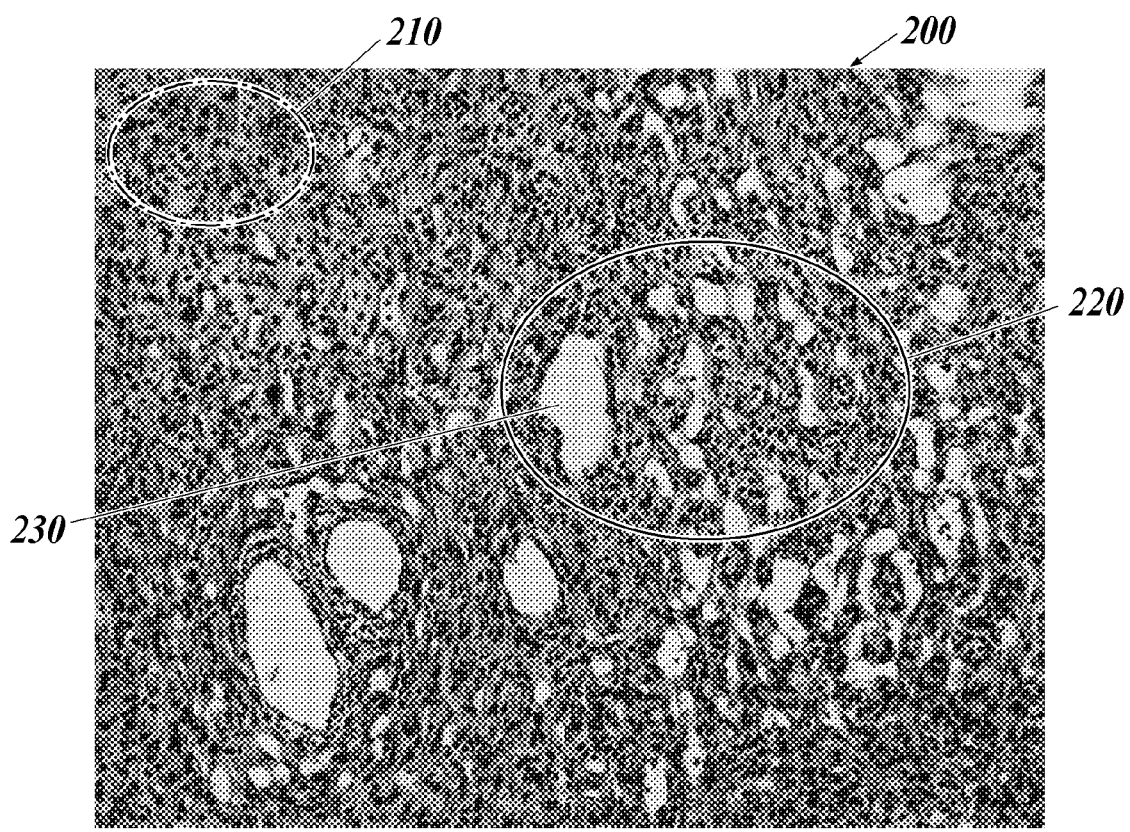
FIG. 8A is an example of a bright-field image.

FIG. 8A shows a bright-field image 200 that is obtained by imaging a tissue sample with a bright-field unit of microscope image-obtaining device 1A. The tissue sample is a tissue section collected from a subject and stained through HE staining. As shown in FIG. 8A, the bright-field image 200 includes a tumor region 210 and an interstitial region 220, and the interstitial region 220 includes a blood vessel 230.

In the tissue section, the target substance (HER2) is stained with phosphor integrated dots. Although not shown, a fluorescent image that has the same field of view as the bright-field image 200 is obtained with the fluorescent unit of the microscope image-obtaining device 1A.

Figure 8B:
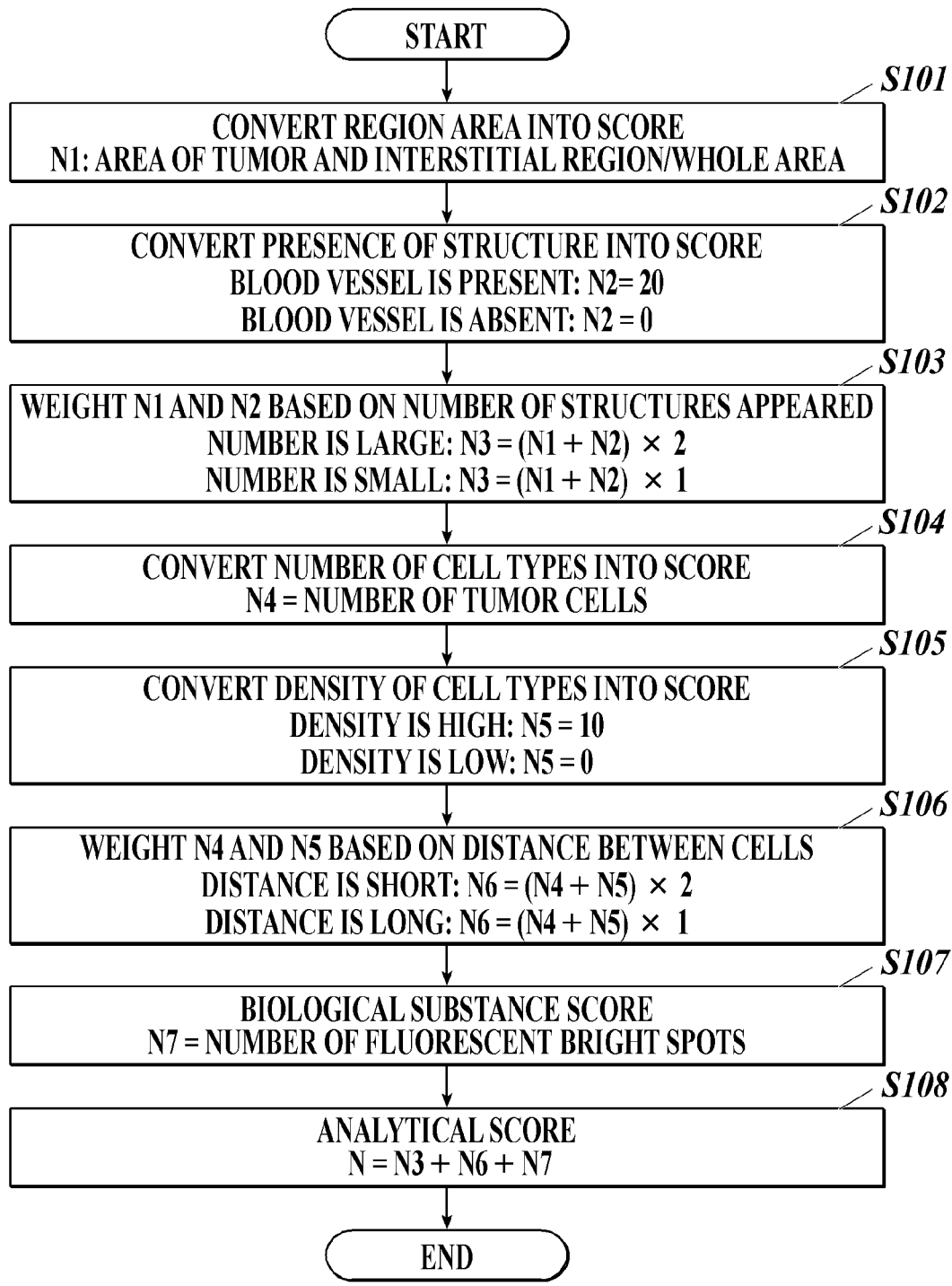
FIG. 8B is an example of a method for calculating an analysis score.

FIG. 8B is a flowchart of calculating an analysis score. Herein, information for creating scores is set and weighting of scores is defined so that desired support information is output for the user. Hereinafter, a method of calculating the analysis score of the example tissue sample in FIG. 8A is described according to the flow shown in FIG. 8B.

First, the region area is scored (step S101). Herein, the ratio of the area of the tumor region 210 and the interstitial region 220 to the whole area of the tissue sample is scored as a score $N1$. $N1$ is the standardized value of the value obtained from the expression: (area of tumor region 210 and interstitial region 220)/(area of bright-field image 200).

From the tissue sample in FIG. 8A, $N1=40$ is obtained.

Next, the presence/absence of structures is scored (step S102). Herein, the presence/absence of blood vessels in the tissue sample is scored as the score $N2$. When a blood vessel(s) is present, $N2$ is 20. When no blood vessel is present, $N2$ is 0.

In the tissue sample of FIG. 8A, a blood vessel 230 is observed in the interstitial region 220. Accordingly, $N2$ is 20.

Next, $N1$ and $N2$ are weighted based on the number of present structures (step S103). Herein, when the number of blood vessels present in the tissue sample is greater than the predetermined number, $N3=(N1+N2)\times 2$ holds. When the number is less than the predetermined number, $N3=(N1+N2)\times 1$ holds.

In the tissue sample of FIG. 8A, the number of blood vessels 230 is greater than the predetermined number. Accordingly, $N3$ is $(N1+N2)\times 2=(40+20)\times 2=120$.

Next, the number of cell types is scored (step S104). Herein, the number of tumor cells in the tissue sample is scored as the score $N4$. $N4$ is obtained by standardizing the number of tumor cells.

From the tissue sample in FIG. 8A, $N4=30$ is obtained.

Next, the concentration of cell types is scored (step S105). Herein, the concentration of tumor cells in the tissue sample is scored as the score $N5$. When the concentration of tumor cells in the tissue sample is greater than the predetermined concentration, $N5$ is 10. When the concentration is less than the predetermined concentration, $N5$ is 0.

In the tissue sample of FIG. 8A, the concentration of tumor cells is greater than the predetermined concentration. Accordingly, $N5$ is 10.

Next, $N4$ and $N5$ are weighted based on the distance between cells (step S106).

Herein, when the distance between the tumor cells in the tumor region 210 and the immune cells in the interstitial region 220 in the tissue sample is shorter than a predetermined distance (cells are close to each other), $N6=(N4+N5)\times 2$ holds. When the distance is longer than the predetermined distance (cells are far from each other), $N6=(N4+N5)\times 1$ holds.

In the tissue sample of FIG. 8A, the distance between cells is shorter than the predetermined distance. Accordingly, $N6$ is $(N4+N5)\times 2=(30+10)\times 2=80$.

Next, the biological substance score $N7$ is calculated (step S108). Herein, the number of bright spots of phosphor integrated dots based on the abundance of the target substance is scored as the score $N7$. The score $N7$ is the standardized value of the number of fluorescent bright spots.

From the tissue sample in FIG. 8A, $N7=50$ is obtained.

The analysis score $N$ is obtained by adding up the scores calculated as described above (step S108). Herein, $N=N3+N6+N7$ holds.

From the tissue sample of FIG. 8A, $N$ is $N3+N6+N7=120+80+50=250$.

This analysis score $N=250$ is presented to the user. For example, when analysis scores are associated with degrees of malignancy of cancer beforehand, the user can refer to the analysis score in judging the degree of malignancy of cancer of the subject. Thus, the analysis score can serve as an index in various judgements, such as pathological diagnosis.

Other Embodiments

The above-described embodiment of the present invention is a preferable example and does not limit the present invention.

In the above description, a HDD and a nonvolatile semiconductor memory are shown as examples of a computer-readable medium that stores the program of the present invention. The computer-readable medium is, however, not limited to these examples. As other computer readable media, a portable storage medium, such as a CD-ROM, can be used. Further, as a medium to provide data of the program of the present invention over a communication line, a carrier wave can be used.

Other detailed configurations and detailed operations of devices constituting the pathological diagnosis support system 100 can also be appropriately modified without departing from the scope of the present invention.

INDUSTRIAL APPLICABILITY

The present invention is applicable to an information provision method, an information provision device, and a program that can provide objective and accurate support information for making various judgments based on information obtained from tissue sections.

REFERENCE SIGNS LIST

100 Pathological diagnosis support system
1A microscope image-obtaining device
2A Information provision device
21 Controller (image obtainer, score calculator, information presenter)
22 Operation receiver
23 Display
24 Communication I/F
25 Storage
N Communication network

The invention claimed is:

1. An information provision method for providing support information, the support information for supporting a judgement based on information obtained from a tissue section, the method comprising:
   obtaining a digital bright-field image of the tissue section stained to be observable in a bright field;
   obtaining multiple kinds of information on the bright-field image;
   staining the tissue section with a staining reagent such that a specific biological substance present in the tissue section is observable with fluorescence;
   obtaining a digital fluorescent image of the tissue section;
   obtaining information on a presence or distribution of the specific biological substance from the fluorescent image;
   creating an analysis score by obtaining and combining scores for the multiple kinds of information on the bright-field image and a biological substance score for the information on the presence or distribution of the specific biological substance from the fluorescent image; and
   presenting the analysis score as the support information,
   wherein the multiple kinds of information on the bright-field image include a region score based on at least one of a tumor region area and an interstitial region area in the tissue section, a structure score based on a structure in the tissue section, the structure being a blood vessel structure, lymphatic vessel structure, or a secretory structure, and a cell type score based on presence of a cell type in the tissue section.

2. The information provision method according to claim 1, wherein the step of obtaining the digital bright-field image includes obtaining the bright-field image of a whole of the tissue section, the bright-field image being captured by a virtual microscope slide-creating device capable of imaging the whole tissue section.

3. The information provision method according to claim 1, wherein
   the multiple kinds of information include information on a positional relationship of a region, the structure, and the cell type present in the tissue section.

4. The information provision method according to claim 1, wherein
   the staining reagent contains phosphor integrated dots bonded with biological substance-recognizing portions, each of the phosphor integrated dots being constituted of multiple integrated fluorescent substances.

5. The information provision method according to claim 1, wherein the steps of staining the tissue section with a staining reagent and obtaining information on the presence or distribution of the specific biological substance include visualizing a specific region of the tissue section by staining the specific biological substance present in the specific region of the tissue section with a fluorescent substance such that the specific biological substance is observable with fluorescence.

6. The information provision method according to claim 1, wherein
   the region score and the structure score are combined and weighted based on a number of structures in the tissue section to form a first weighted score, and
   the cell type score is weighted based on a distance between a cell of the cell type in the tumor region and an immune cell in the interstitial region to form a second weighted score.

7. The information provision method according to claim 6, wherein the analysis score is a sum of the first weighted score, the second weighted score, and the biological substance score.

8. An information provision device that provides support information for supporting a judgement based on information obtained from a tissue section, the device comprising a hardware processor that:
   obtains a digital bright-field image of the tissue section stained to be observable in a bright field;
   obtains multiple kinds of information on the bright-field image;
   obtains a digital fluorescent image of the tissue section after the tissue section is stained with a staining reagent such that a specific biological substance present in the tissue section is observable with fluorescence;
   obtains information on a presence or distribution of the specific biological substance from the fluorescent image;
   creates an analysis score by obtaining and combining scores for the multiple kinds of information on the bright-field image and a biological substance score for the information on the presence or distribution of the specific biological substance from the fluorescent image; and
   presents the analysis score as the support information,
   wherein the multiple kinds of information on the bright-field image include a region score based on at least one of a tumor region area and an interstitial region area in the tissue section, a structure score based on a structure in the tissue section, the structure being a blood vessel structure, lymphatic vessel structure, or a secretory structure, and a cell type score based on presence of a cell type in the tissue section.

9. A non-transitory computer-readable storage medium storing a program for a computer of an information provision device that provides support information for supporting a judgement based on information obtained from a tissue section, the program causing the computer to perform:
   obtaining a digital bright-field image of the tissue section stained to be observable in a bright field;
   obtaining multiple kinds of information on the bright-field image;
   obtaining a digital fluorescent image of the tissue section after the tissue section is stained with a staining reagent such that a specific biological substance present in the tissue section is observable with fluorescence;

obtaining information on a presence or distribution of the specific biological substance from the fluorescent image;

creating an analysis score by obtaining and combining scores for the multiple kinds of information on the bright-field image and a biological substance score for the information on the presence or distribution of the specific biological substance from the fluorescent image; and presenting the analysis score as the support information, wherein the multiple kinds of information on the bright-field image include a region score based on at least one of a tumor region area and an interstitial region area in the tissue section, a structure score based on a structure in the tissue section, the structure being a blood vessel structure, lymphatic vessel structure, or a secretory structure, and a cell type score based on presence of a cell type in the tissue section.

* * * * *